United States Patent [19]

Fenyes et al.

[11] Patent Number: 5,225,432
[45] Date of Patent: Jul. 6, 1993

[54] CONTROL OF MICRO-ORGANISMS ON PLANTS WITH 1-HYDROXYMETHYLPYRAZOLES

[75] Inventors: Joseph G. Fenyes, Germantown; Miguel L. Pulido, Memphis, both of Tenn.

[73] Assignee: Buckman Laboratories International, Inc., Memphis, Tenn.

[21] Appl. No.: 803,722

[22] Filed: Dec. 9, 1991

Related U.S. Application Data

[63] Continuation of Ser. No. 555,035, Jul. 20, 1990, abandoned.

[51] Int. Cl.$^5$ .................. A01N 43/56; A01N 43/50
[52] U.S. Cl. .......................... 514/407; 514/406; 514/404; 514/403
[58] Field of Search ............ 514/342, 403, 406, 404, 514/407

[56] References Cited

U.S. PATENT DOCUMENTS

| | | | |
|---|---|---|---|
| 3,409,632 | 11/1968 | Fenyes | 548/373.1 |
| 3,577,545 | 5/1971 | Fenyes | 514/407 |
| 4,801,362 | 1/1989 | Fenyes | 252/51 |
| 4,966,908 | 10/1990 | Eckhardt | 514/340 |

FOREIGN PATENT DOCUMENTS 0008056 2/1980 European Pat. Off. .
7040465 6/1982 Japan .

Primary Examiner—Frederick E. Waddell
Assistant Examiner—Gregory Hook
Attorney, Agent, or Firm—Finnegan, Henderson, Farabow, Garrett & Dunner

[57] ABSTRACT

A method of protecting plants and seeds thereof which are susceptible to attack by microorganisms. To the plant or seed is applied a compound having the formula

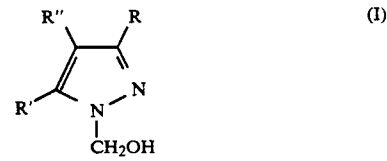

wherein R and R' are independently selected from hydrogen and alkyl of 1 to 4 carbon atoms; and R" is a moiety selected from the group consisting of (a) hydrogen, (b) a halogen atom selected from the group consisting of F, Cl, Br and I, and (c) a nitro group or the hydrochloride salt of the compound. The method disclosed is especially useful for protecting ornamental plants, vegetable plants and cereal crop plants and seeds thereof which are susceptible to attack by microorganisms. A composition containing the compound of formula I for use in protecting plants which are susceptible to attack by microorganisms is also provided.

10 Claims, No Drawings

CONTROL OF MICRO-ORGANISMS ON PLANTS WITH 1-HYDROXYMETHYLPYRAZOLES

This application is a continuation of application Ser. No. 07/555,035, filed Jul. 20, 1990, now abandoned.

BACKGROUND OF THE INVENTION

Field of the Invention

The subject of the present invention is directed to a method and composition for the control of microorganisms on plants. More particularly, the present invention relates to the use of certain 1-hydroxymethylpyrazoles as an agricultural microbicide, especially as a bactericide or fungicide.

SUMMARY OF THE INVENTION

The present invention provides a method for the control of microorganisms, including but not limited to bacteria and fungi, comprising the step of applying to a plant or the seed thereof an amount sufficient to inhibit the growth and proliferation of at least one microorganism on the plant or seed of a compound having the formula I

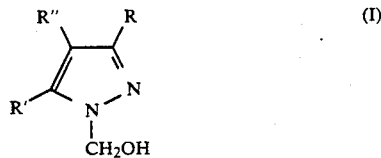

wherein R and R' are independently selected from hydrogen and alkyl of 1 to 4 carbon atoms, R" is a moiety selected from the group consisting of (a) hydrogen, (b) a halogen atom selected from the group consisting of F, Cl, Br and I, and (c) a nitro group, or the hydrochloride salt of said compound.

The applying step may be accomplished by spraying a composition comprising a compound of formula I. A sufficient amount of the compound of the formula I can be in the range of about 2,500 to about 30,000 ppm of the composition, and preferably in the range of about 15,000 to about 25,000 ppm of the composition. The compound can be 3,5-dimethyl-1-hydroxymethylpyrazole or 3,5-dimethyl-1-hydroxymethylpyrazole hydrochloride. The microorganisms can be bacteria and fungi. The bacteria can be *Erwinia caratovora*, Agrobacteria sp., coryne-bacteria, Xanthomonas sp., Pseudomonas sp., *Escherichia coli, Staphylococcus aureus* and *Pseudomonas aeruginosa*. The fungi can be *Pythium ultimum, Helminthosporium sativum, Rhizoctonia solani, Monilia fructicola, Fusarium oxysporum, Peronospora parasitica* and *Alternaria solani*. The plant or seed can be ornamental plants, fruit plants, vegetable plants, cereal crop plants and seeds thereof. The application of the compound or hydrochloride salt to the plant or seed can be done two or more times.

A composition is also provided which includes an amount per unit weight of the compound of formula I sufficient to inhibit the growth and proliferation of at least one microorganism on the plant, together with an inert carrier. The compound can be 3,5-dimethyl-1-hydroxymethylpyrazole or 3,5-dimethyl-1-hydroxymethylpyrazole hydrochloride. The composition can include at least one inert additive relative to the compound of formula I, and the additive can be from stabilizers, spreading agents, wetting agents, sticking agents, fillers, bactericides, fungicides, pesticides, and any combination thereof. The combination can be in the form of a solution of dispersion with the carrier being inert relative to the compound of formula I, and can be liquid and powders. For example, the carrier can be water or a flowable powder.

DESCRIPTION OF THE PREFERRED EMBODIMENTS

For purposes of the present invention, the term "microorganism" is intended to include but is not limited to bacteria, fungi and yeasts, and is intended to include but is not limited to phytopathogens within these families.

The method and composition of the invention may be used to prevent attacks by at least one microorganism on plants, including but not limited to ornamental plants, fruit plants, vegetable plants and cereal crop plants and seeds thereof. Ornamental plants can include orchids and roses; fruit plants can include orange trees and pear trees; vegetable plants can include cauliflower, tomatoes and onion plants. Bactericidally or fungicidally effective amounts of the compound of formula I can be alternatively applied to the bacteria, the fungi or the respective hosts, particularly hosts like plants, plant seeds, paper and the like, which are attacked by these microorganisms.

The bactericidal and fungicidal activities of the compounds of the invention are surprising in so far as N-methyl compounds of similar stability, for example, N-hydroxy-methylphthalimide, are not very effective with regard to their antimicrobial and preservative activity.

The compounds of this invention may be prepared by reacting either solid paraformaldehyde or an aqueous formaldehyde solution with a pyrazole derivative. Preferred methods of preparation are given in Dvoretzky et al., *Formaldehyde Condensation in the Pyrazole Series*, 15 Journ. Org. Chem 1285–8 (1952) and Huttel et al., *Mannichsche Reaktion der Pyrazole*, 85 Chemsiche Berichte 820–26 (1952), both hereby specifically incorporated by reference. Another preferred method of preparation is given in an application of Fenyes and Pulido entitled "Process for the Preparation of 1-Hydroxymethylpyrazoles", filed Jul. 20, 1990, concurrently herewith, which is hereby specifically incorporated by reference.

The antimicrobial activity of the compounds used in accordance with the invention extends to a variety of different microorganisms, including but not limited to bacteria such as *Erwinia caratovora*, Agrobacteria sp., corynebacteria, Xanthomonas sp., Pseudomonas sp., *Escherichia coli, Staphylococcus aureus* and *Pseudomonan aeruginosa*, and including but not limited to fungi such as *Pythium ultimum, Helminthosporium sativum, Rhizoctania solani, Fusarium oxysporum, Monilia fructicola, Peronospora parasitica* and *Alternaria solani.*

The preferred compounds of this invention include 3,5-dimethyl-1-hydroxymethylpyrazole, or the hydrochloride salt thereof, which generally exhibit relatively increased bactericidal and fungicidal activity under identical conditions over the 3,5-dimethyl-4-substituted-1-hydroxymethylpyrazoles in accordance with the invention.

The pyrazoles of this invention may be formulated and applied in bactericidal or fungicidal amounts, as the case may be, by conventional art methods. The compounds of formula I are preferably used in a composition with one or more inert liquid or solid carriers or excipients such as powders, solutions and dispersions, most preferably in a spray with water or a flowable powder. Compositions of these pyrazoles may also contain compatible stabilizers, spreading agents, wetting agents, sticking agents, fillers, other bactericides, other fungicides, pesticides and the like, and combinations thereof.

The concentration of the compounds used in accordance with the invention which inhibits growth and proliferation of at least one microorganism, and thus provides the antimicrobial activity described herein, may be readily determined by one skilled in the art without extensive experimentation. Factors affecting concentration include but are not limited to weather conditions, the type of plant(s) and the type of microorganism(s) present. An effective dosage may possibly be as low as about 2500 parts per million (ppm) (about 0.5% weight per volume water solution basis), will range from about 2500 ppm to about 30,000 ppm (about 3.0%), preferably in the range from about 15,000 (about 1.5%) ppm to about 25,000 ppm (about 2.5%). One or more applications of the compound may be undertaken, as required, with factors affecting frequency of application including but not limited to weather conditions, the type of plant(s), and the type of microorganism(s) present.

To illustrate the nature of the invention, the following examples are given. It should be understood, however, that the invention is not to be limited to the specific conditions or details set forth in these examples.

EXAMPLE 1

The bacterial effectiveness of these compounds was demonstrated in bacterial suspensions prepared by washing a culture of the desired bacteria from agar slant with sterile water into a vessel and further diluting the aqueous suspension to 250 μL with sterile water. The test was conducted as follows:

The pyrazole to be tested was dissolved in acetone to 500 ppm and 30 μL of this solution was pipetted onto each of two surface areas on a plate covered with 20 mL of Emerson's agar. The treated agar plates were then sprayed with the bacteria suspension and the plates were incubated for 44 to 48 hours at 24° C. The two treated areas of the plate were then observed for bacterial growth. The pyrazole's effectiveness for controlling bacterial growth in the treated areas was rated as "+" or "−"; with the plus sign (+) indicating the areas were completely free of bacterial growth and with the minus sign (−) indicating they were completely overgrown. The results of this comparative bactericidal test appear in Table I.

TABLE I

| | Effectiveness | |
|---|---|---|
| Compound | Erwinia caratovora | Pseudomonas syringae |
| 3,5-dimethyl-1-hydroxy methylpyrazole | + | + |
| 3,5-dimethyl-4-chloro-1-hydroxylmethylpyrazole | + | + |
| 3,5-dimethyl-4-nitro-1-hydroxymethylpyrazole | − | + |

EXAMPLE 2

The mycelial drop method was used to test fungicidal activity. This method measures the fungitoxicity of a compound in terms of its inhibition of fungus mycelial growth. The general procedure was as follows: Each pyrazole to be tested was dissolved in acetone to a 100 ppm up to 15,000 ppm concentration. Equal volumes of these solutions were applied to the centers of each of three replicate paper discs inoculated with the desired fungus mycelium and placed on potato-dextrose agar medium.

Following this application, the discs were incubated along with inoculated but untreated control discs at ambient temperatures until the control discs were filled with mycelial growth. The fungicidal activity of the pyrazole was determined by comparing the radii of mycelial growth away from the edges of the treated and control discs. From this comparison a percent inhibition based on the relative mycelial growth areas was determined. The results of this comparative fungicidal test at two selected concentrations appear below in Table II.

EXAMPLE 3

The slide spore germination method was also used to test fungicidal activity. This method is described in the *American Phytopathological Society Journal*, Vol. 33, pages 627–632 (1943), and measures the fungitoxicity of compounds in terms of their percent inhibition of fungus spores. The general procedure was as follows: Each pyrazole to be tested was dissolved in acetone to several concentrations between 50 ppm up to 15,000 ppm. These solutions were then pipetted into the wells of depression slides and allowed to dry. The wells were filled with a spore suspension of the specified test organism and incubated in a moist chamber overnight. A group of 100 spores was examined and the numbers of spores germinated and not germinated were counted in separate tallies and recorded to show the biological activity in terms of the percentage inhibition. The results of this comparative fungicidal test at two selected concentrations also appear in Table II.

TABLE II

| Concentration (ppm) | Compound | Percent Inhibition | | | | |
|---|---|---|---|---|---|---|
| | | Mycelial Drop | | | Slide Spore | |
| | | P | H | R | M | A |
| 500 | 3,5-Dimethyl-1-hydroxymethylpyrazole | 100 | 97 | 90 | 100 | 100 |
| 1000 | 3,5-Dimethyl-1-hydroxymethylpyrazole | 100 | 100 | 100 | 100 | 100 |

P = *Pythium ultimum*
H = *Helminthosporium sativum*
R = *Rhizoctonia solani*
M = *Monilia fructicola*
A = *Alternaria solani*

EXAMPLE 4

Other pyrazoles of this invention were tested by the mycelial drop method as described above in Example 2, except that these pyrazoles were dissolved in acetone to a concentration of 500 ppm. The results of this comparative fungicidal test appear in Table III.

TABLE III

| | Percent Inhibition | | | |
|---|---|---|---|---|
| Compound | P | H | F | R |
| 3,5-dimethyl-4-chloro-1-hydroxymethylpyrazole | 100 | 85 | 90 | 70 |
| 3,5-dimethyl-4-bromo-1-hydroxymethylpyrazole | 100 | 90 | 95 | 90 |
| 3,5-dimethyl-4-iodo-1- | 90 | 75 | 75 | 75 |

TABLE III-continued

| Compound | Percent Inhibition | | | |
|---|---|---|---|---|
| | P | H | F | R |
| hydroxymethylpyrazole 3,5-dimethyl-4-nitro-1-hydroxymethylpyrazole | 90 | 85 | 75 | 85 |

P = *Pythium ultimum*
H = *Helminthosporium sativum*
F = *Fusarium oxysporum*
R = *Rhizoctonia solani*

EXAMPLE 5

A composition in accordance with the invention comprising a water solution containing 1.5 percent (about 15,000 ppm) on a weight by volume basis of a compound containing 98.0 percent on a weight by weight basis of 1-hydroxymethyl-3,5-dimethylpyrazole was prepared by dissolving 30 grams of the compound (technical grade) in 20 liters of water.

Cauliflower was planted in a 0.04 hectare field following the standard agricultural practice for this vegetable. When the heads were being formed, the stems became infested with *Erwinia caratovora*. This bacterium is the causal agent of soft rot, and produces an enzyme which interacts with the middle lamella of the host tissue. The cells in the older decayed tissue eventually become plasmolyzed. All of these effects result in soft rot.

The cauliflower was sprayed with the aforementioned composition until liquid ran off of the foliage. Three days later, the soft rot wounds were observed to be dried, an indication that the Erwinia bacterium was no longer active. The treated plants were observed to be recovered completely. Furthermore, no phytotoxicity was induced on the cauliflower plant by spraying this composition. The degree of infection in the cauliflower by the Erwinia bacterium was recorded on the basis of the following key:

| | |
|---|---|
| Very severe bacterial infection/abundant soft rot tissue in cauliflower stems | 5 |
| Severe bacterial infection | 4 |
| Moderate bacterial infection | 3 |
| Slight bacterial infection | 2 |
| Soft rot host-tissue became dried | 1 |
| Absence of bacterial infection/host tissue wounds dried and plants recovered | 0 |

The results of this test are summarized in the following Table IV:

TABLE IV

| Treatment | Dosage | Average Rating of Disease Incidence After Spraying | |
|---|---|---|---|
| | | 3 days | 10 days |
| Untreated Control | 0 | 5 | 5 |
| Treated with Composition | 1.5% solution | 1 | 0 |

EXAMPLE 6

A composition in accordance with the invention containing 5 percent on a weight by volume basis of the active compound in water as in Example 5 was prepared by dissolving 100 grams of the technical grade of the compound in 20 liters of water.

This 5 percent composition was then sprayed to run-off on the foliage of cauliflower plants growing in standard producing fields. No phytotoxicity was observed as the result of spraying with this 5 percent solution.

EXAMPLE 7

Two species of orchids were infected with Pseudomonas sp. These two orchids were: Dendrobium and Oncidium. The infected orchid plants were sprayed to foliage run-off with a 1.5 percent composition of the active compound as prepared in Example 5. Readings were taken at 3 and 7 days after spraying. No phytotoxicity was observed as the result of spraying with this 1.5 percent solution. The results obtained were recorded on the basis of the following key:

| | |
|---|---|
| Very severe bacterial infection | 5 |
| Severe bacterial infection | 4 |
| Moderate bacterial infection | 3 |
| Slight bacterial infection | 2 |
| Very slight bacterial infection | 1 |
| No bacterial infection | 0 |

The results of this test for both orchid species were equivalent and are summarized in the following Table V. This test may indicate a need to test larger dosages for Pseudomonas sp. control on orchids.

TABLE V

| Treatment | Dosage | Average Rating of Disease Incidence After Spraying | |
|---|---|---|---|
| | | 3 days | 10 days |
| Untreated Control | 0 | 4 | 4 |
| Treated with Composition | 1.5% solution | 2 | 3 |

EXAMPLE 8

A cauliflower field infested with the fungus *Peronospora parasitica* was sprayed with the 1.5 percent composition as prepared in Example 5. The Peronospora fungus attacks the foliage and cauliflower head producing sunken dark spots (small to larger than one inch), which make the agricultural product unfit for human consumption. Three days after spraying, the infested areas were observed to have died. No phytotoxicity was observed by spraying with the composition.

The disease incidence in the cauliflower was recorded on the basis of the following key:

| | |
|---|---|
| Severe disease incidence | 3 |
| Moderate disease incidence | 2 |
| Slight disease incidence | 1 |
| Disease incidence controlled | 0 |

The following Table VI summarizes the results of this test:

TABLE VI

| Treatment | Dosage | Average Disease Rating | |
|---|---|---|---|
| | | Before Spraying | 3 Days After Spraying |
| Untreated Control | 0 | 3 | 3 |
| Treated with Composition | 1.5% solution | 3 | 0 |

EXAMPLE 9

A composition containing 1-hydroxymethyl-3,5-dimethylpryazole was tested for controlling fungal and bacterial diseases interfering with cabbage seed germination. The Aspergillus sp. and bacteria are known to affect seed germination and vigor. The same amount of seed was soaked for 10 minutes in different treatments. The seed was then sprayed on tissue paper and its germination was observed. Temperature and water conditions were maintained constant for all the treatments in this germination test. The results of this test were recorded on basis of seed germination and seedling vigor based on the following key:

| | |
|---|---|
| Excellent germination/vigor | 3 |
| Good germination/vigor | 2 |
| Poor germination/vigor | 1 |
| No germination | 0 |

It should be noted that seedling vigor is considered an index of the treatment phytotoxicity, and on this basis, no phytotoxicity was observed. The following Table VII summarizes the results of this test:

TABLE VII

| Treatment | Dosage | Soaking Time | Germination Rating | Sprouting Days After Seeding days |
|---|---|---|---|---|
| Untreated Seed | — | 0 | 1 | 5 |
| Hot Water At 55° C. | — | 10 mins. | 3 | 2 |
| Treated with Composition | 0.5% solution | 10 mins. | 3 | 5 |

What is claimed is:

1. A method for controlling microorganisms on a plant comprising applying to a plant selected from an ornamental plant, a fruit plant, a vegetable plant or a cereal crop plant or the seed thereof an amount sufficient to inhibit the growth and proliferation of at least one microorganism on said plant or seed of a compound of the formula I

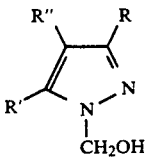

wherein R and R' are independently selected from hydrogen and an alkyl of 1 to 4 carbon atoms, and R" is a moiety selected from the group consisting of (a) hydrogen, (b) a halogen atom selected from the group consisting of F, Cl, Br and I, and (c) a nitro group, or the hydrochloride salt of said compound.

2. The method of claim 1, wherein said applying comprises spraying a composition comprising the compound of formula I.

3. The method of claim 2, wherein said sufficient amount is in the range of about 2,500 to about 30,000 parts per million of said composition.

4. The method of claim 3, wherein said sufficient amount is in the range of about 15,000 to about 25,000 parts per million of said composition.

5. The method of claim 1, wherein said compound is 3,5-dimethyl-1-hydroxymethylpyrazole.

6. The method of claim 1, wherein said compound is 3,5-dimethyl-1-hydroxymethylpyrazole hydrochloride.

7. The method of claim 1, wherein said microorganism is selected from the group consisting of bacteria and fungi.

8. The method of claim 7, wherein said microorganism is a bacteria selected from the group consisting of *Erwinia caratovora*, agrobacteria, corynebacteria, Xanthomonas sp., Pseudomonas sp., *Escherichia coli, Staphylococcus aureus* and *Pseudomonas aeruginosa.*

9. The method of claim 7, wherein said microorganism is a fungus selected from the group consisting of *Pythium ultimum, Helminthosporium sativum, Rhizoctonia solani, Monilia fructicola, Fusarium oxysporum, Peronospora parasitica* and *Alternaria solani.*

10. The method of claim 1, comprising applying said compound or hydrochloride salt to said plant or seed two or more times.

* * * * *